US008649890B2

(12) United States Patent
Martin (10) Patent No.: US 8,649,890 B2
(45) Date of Patent: Feb. 11, 2014

(54) SYSTEM AND METHOD FOR PROVIDING AN ATHLETE WITH A PERFORMANCE PROFILE

(76) Inventor: Todd M. Martin, Calabasas, CA (US)

( * ) Notice: Subject to any disclaimer, the term of this patent is extended or adjusted under 35 U.S.C. 154(b) by 0 days.

(21) Appl. No.: 13/484,213

(22) Filed: May 30, 2012

(65) Prior Publication Data

US 2012/0310389 A1     Dec. 6, 2012

Related U.S. Application Data

(60) Provisional application No. 61/491,325, filed on May 31, 2011.

(51) Int. Cl.
*G06F 19/00*     (2011.01)

(52) U.S. Cl.
USPC ............................................. 700/91; 700/92

(58) Field of Classification Search
USPC ....................................... 700/91–92
See application file for complete search history.

(56) References Cited

U.S. PATENT DOCUMENTS

| | | | | |
|---|---|---|---|---|
| 6,013,007 A * | 1/2000 | Root et al. | ......................... | 482/8 |
| 6,608,563 B2 * | 8/2003 | Weston et al. | ............. | 340/573.1 |
| 6,985,875 B1 * | 1/2006 | Wolf | .......................... | 705/26.62 |
| 7,047,214 B2 * | 5/2006 | Wolf | ............................. | 705/26.8 |
| 7,158,689 B2 * | 1/2007 | Valleriano et al. | ............. | 382/278 |
| 7,254,516 B2 * | 8/2007 | Case et al. | .................... | 702/182 |
| 7,800,646 B2 * | 9/2010 | Martin | ........................... | 348/157 |
| 7,876,352 B2 * | 1/2011 | Martin | ........................... | 348/157 |
| 7,934,983 B1 * | 5/2011 | Eisner | ............................... | 463/6 |
| 2004/0201738 A1 * | 10/2004 | Moores et al. | ............. | 348/231.2 |
| 2006/0064731 A1 * | 3/2006 | Kahle et al. | .................... | 725/105 |
| 2006/0125930 A1 * | 6/2006 | Mindrum et al. | .......... | 348/211.3 |
| 2006/0235765 A1 * | 10/2006 | David | ............................ | 705/27 |
| 2006/0287930 A1 * | 12/2006 | Wolf et al. | ....................... | 705/26 |
| 2007/0118239 A1 * | 5/2007 | Zimmermann et al. | ........ | 700/92 |
| 2008/0052349 A1 * | 2/2008 | Lin | ................ | 709/203 |
| 2009/0141138 A1 * | 6/2009 | DeAngelis | ................. | 348/220.1 |
| 2010/0004097 A1 * | 1/2010 | D'Eredita | ......................... | 482/8 |
| 2010/0149305 A1 | 6/2010 | Catchpole et al. | | |
| 2010/0191827 A1 | 7/2010 | Martin | | |
| 2010/0210421 A1 * | 8/2010 | Case et al. | ......................... | 482/8 |
| 2011/0250937 A1 * | 10/2011 | Hubbard et al. | .................. | 463/6 |
| 2012/0253485 A1 * | 10/2012 | Weast et al. | ...................... | 700/91 |
| 2012/0290109 A1 * | 11/2012 | Engelberg et al. | .............. | 700/91 |

OTHER PUBLICATIONS

Earthday 5K Run [online]. Jun. 16, 2010[retrieved Apr. 30, 2013]. Retrieved from the Ineternet: <URL: http://web.archive.org/web/20100616133511/http://www.compuscore.com/cs2010/april/earthday.htm>.*

(Continued)

*Primary Examiner* — Dmitry Suhol
*Assistant Examiner* — David Duffy
(74) *Attorney, Agent, or Firm* — Todd M. Martin (57) ABSTRACT

A web-based platform and method for providing access to information regarding athletic events and personal training information. The platform may include an events calendar that may be personalized, a training log, a media portal containing photographs of a participant in an athletic event, and a rankings generator configured to rank a user against other users within given set of parameters.

24 Claims, 9 Drawing Sheets

(56) References Cited

OTHER PUBLICATIONS

USA Triathlon—FAQ [online]. May 11, 2009 [retrieved Jun. 18, 2013]. Retreived from the Internet: <URL: http://web.archive.org/web/20090511172916/http://triathlon.teamusa.org/content/index/666>.*

Ritchie, Jody. 2007 Final Rankings Men's Tri [online]. Nov. 3, 2008 [retreived Jun. 18, 2013]. Retrieved from the Internet: <URL: http://www.usatriathlon.org/~/media/72112382b8294b86af210005a3f8e03b.ashx>.*

Further Examination Report dated May 8, 2013 for New Zealand Application No. 600383 (2 pages).

Further Examination Report dated Jul. 1, 2013 for New Zealand Application No. 600383 (1 page).

* cited by examiner

FIG. 1

|  | Racing Calendar | | | |
|---|---|---|---|---|
| Select | Date | Event | Location | Contact |
| ☐ | 6/4/11 | 5k | Zuma | Todd |
| ☑ | 6/4/11 | 10k | Sydney | Natasha |
| ☐ | 6/4/11 | 5k | LA | Race Management Inc. |

FIG. 2

| June | | | | | | |
|---|---|---|---|---|---|---|
| S | M | T | W | Th | F | S |
|  |  |  | 1 | 2 | 3 | 4 Sydney 10k |
| 5 | 6 | 7 | 8 | 9 | 10 | 11 |
| 12 | 13 | 14 | 15 | 16 | 17 | 18 |
| 19 | 20 | 21 | 22 | 23 | 24 | 25 |

Create New Route — 128

Activity ▽
- Running
- Cycling
- Swimming

Route Title

Route Description

[Save]

*FIG. 6*

Equipment Tracker — 130

Running
- ☑ Shoes
  - Brand
  - Date of first use
  - Notes
  - Warning Distance
- ☐ Orthotics Cycling
- ☐ Bike
- ☐ Chain
- ☐ Tires
- ☐ Distance since last tune-up Swimming
- ☐ Goggles
- ☐ Wet Suit

FIG. 13

SYSTEM AND METHOD FOR PROVIDING AN ATHLETE WITH A PERFORMANCE PROFILE

This application claims the benefit of U.S. Provisional Application No. 61/491,325, filed May 31, 2011, the entire disclosure of which is incorporated by reference herein.

FIELD OF THE INVENTION

The present invention relates to improvements in a system for storing training data entered by an athlete, associating information with the athlete that is related to the athlete's participation in training and/or racing activities, and generating a profile specific to the athlete.

BACKGROUND OF THE INVENTION

Systems exist which permit a runner to record a distance trained in electronic form to track a total distance run over a given period of time. Such systems are limited in the amount of features they offer, and consequently, the type and amount of performance data they generate. In order to gain a competitive edge, athletes often need access to a variety of key training information in order to enhance fitness. The present invention in one preferred embodiment seeks to provide an athlete with relevant information in order to enhance the athlete's fitness.

SUMMARY

The present invention in one preferred aspect is directed to a web-based platform tailored to providing access to information regarding athletic or sporting events and personal training information. The system may include an events calendar, which is personalizable, a training log, a media portal containing photos of a participant in an event, and a rankings generator configured to rank a user against other users within given set of parameters.

As used herein, "configured" includes creating, changing, or modifying a program on a computer or network of computers so that the computer or network of computers behave according to a set of instructions. The programming to accomplish the various embodiments described herein will be apparent to a person of ordinary skill in the art after reviewing the present specification, and for simplicity, is not detailed herein.

It will be appreciated that in one or more embodiments, the system may include one or more work stations at a back end for use by a platform operator, one or more local client computers for access by users, and a communications network that facilitates communication between the platform, the work stations at the back end, and the client computers. Preferably, the work stations and client computers will include a display and means for entering information, such as a keyboard and/or voice activated data entry. Means for accessing the platform by users may include, but is not limited to personal computers and mobile devices such as tablets and smartphones, and other user devices capable of communicating over a communications network such as the Internet.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE DRAWINGS

Reference will now be made in detail to the present preferred embodiments of the invention, examples of which are illustrated in the accompanying drawings.

Figure 1:
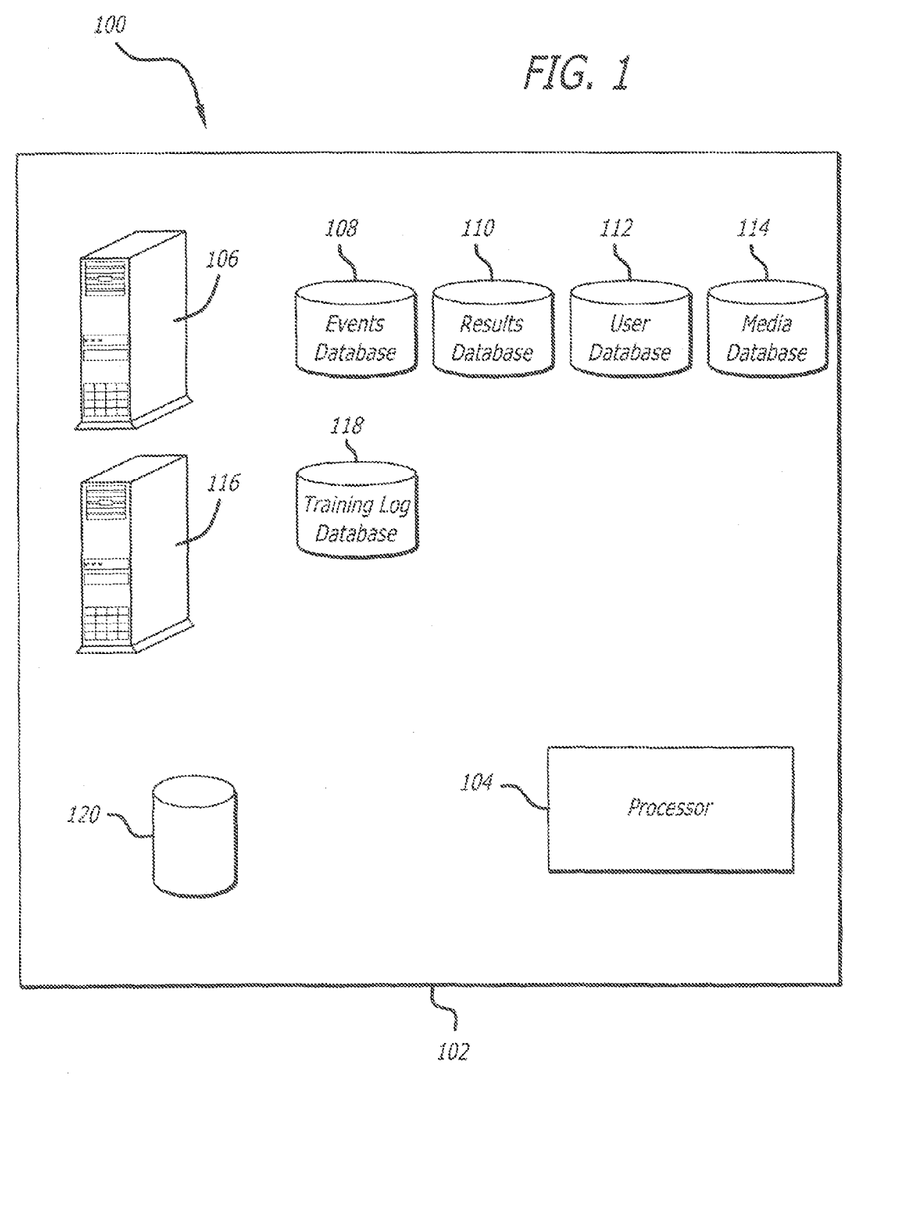
FIG. 1 is a diagram of system components in accordance with a preferred embodiment of the present invention.

FIG. 1 shows a preferred embodiment of a system 100 that includes a computer web-based platform 102 for preferably providing a user with access to an array of information regarding upcoming event information, event results, rankings information and media pertinent to the user's participation in a given event. Platform 102 preferably includes a processor 104, a database server 106 for maintaining an events database 108 that includes a listing of athletic events, a results database 110 that includes results of athletic competitions, a user database 112 that includes records of registered users, a media database 114, a training log server 116, a training log database 118, and a rankings generator 120. The preferred components of platform 102 and their interaction with each other are described further below.

Platform 102 is preferably a computer web-based system accessible by content providers and users. Content providers are preferably individuals or entities that upload or otherwise provide content or data to the platform relating to one or more athletic events. Content may include, but is not limited to results from athletic competitions and media content such as photographs or video from third party providers. As used herein, a third party is an entity that provides content on a commercial basis. Athletic events may include, but are not limited to running races, bike races, swim meets, triathlons, duathlons and other competitions pitting an individual or team against other individuals or teams. Users are preferably individuals or entities desiring access to the content provided by the content providers. Such users may include an individual interested in an upcoming event, a race result, and/or media pertaining to an event. Users may also include individuals who supply data to the platform pertaining to their training in order to generate a training log. In the examples that follow, the platform will be described for use with athletic events relating to running, swimming, biking, triathlons and duathlons. It will be appreciated that the platform may be modified for other athletic events as desired.

Platform 102 preferably includes multiple features accessible by content suppliers and users. For example only, platform 102 preferably includes an events calendar 122, a results page, a training log 124, a rankings generator 120 and a media portal. To facilitate access to these and other features, database server 106 preferably maintains multiple databases of information.

Information for events calendar 122 is preferably maintained in event database 108. Database 108 preferably includes data for each event. Such data may include, but is not limited to category of event (e.g., running, biking, swimming, triathlon), sub-category of event (e.g., for running, 5K, 10K, half-marathon, etc.), date and time, location, contact information and registration details, which may include a link to a site where a user may register for the event.

Information for the results page is preferably maintained in results database 110. Database 110 preferably includes records of results for specified events. Such records may be organized by event name, event category, event sub-category, date, geographic area, and/or event organizer or sub-contractor. Each record preferably contains the results of all participants who complete the competition. Such results may be organized by gender, over-all placing, placing within a predetermined age group, and/or geographic area (e.g., residence of a participant).

Information relating to user access is preferably maintained in user database 112. Database 112 preferably includes records of registered users. Each record preferably includes a record identifier; personal details of the user, such as name, address, gender and age; and access level, for example, cost-free access or subscription level access. Database 112 is useful for when a user accesses the platform and desires to access particular information which may be restricted depending upon the level of access of the user.

To facilitate access to the platform features, platform 102 preferably includes a processor 104 programmed to determine a content supplier or user's access to the platform. Access to platform 102 is preferably determined by whether an individual or entity is a platform operator, content supplier and/or a user. A platform operator has access to the entire platform. On the supply side of the platform, a content supplier may have access to create a record relating to an athletic event for listing in the events calendar. A content supplier may also have access to upload event data such as race results, or media information such as photographs of a participant.

On the consumer side of the platform, a user may have several levels of access. For example only, a user may have unrestricted access to some features of platform 102, such as the events calendar. Other features of the platform may be configured for restricted access, which require a user to register with the platform by providing log-in details, for example, a user name and password. The log-in details are preferably stored in user database 112 and assigned a record identifier. Additional features of platform 102 may be configured for access only by users who are subscribers, i.e., pay a fee for access. Examples of restricted access features may include results data and/or media data. Examples of subscription-only features may include rankings data. Subscribers may be given access to all features of platform 102, while registered users may be given access only to unrestricted features and restricted features that are not subscriber-only features. It will be appreciated that the levels of access may be varied from feature to feature as desired.

Processor 104 is preferably configured to receive a request for access by a user and determine whether the access is restricted. If access is restricted, Processor 104 preferably requests the user to log in, or create a login if the user is a new user. Once processor 104 has determined that the user is a registered user (i.e., the user has provided or created a correct login), the registered user is granted access to the restricted access features of platform 102. If the feature requires a subscription-only access, processor 104 will grant access to the user upon a determination that the user is a subscriber. Additionally, processor 104 may offer the registered user an opportunity to become a subscriber if the registered user attempts to access a subscription-only feature and is not a subscriber.

Figure 2:
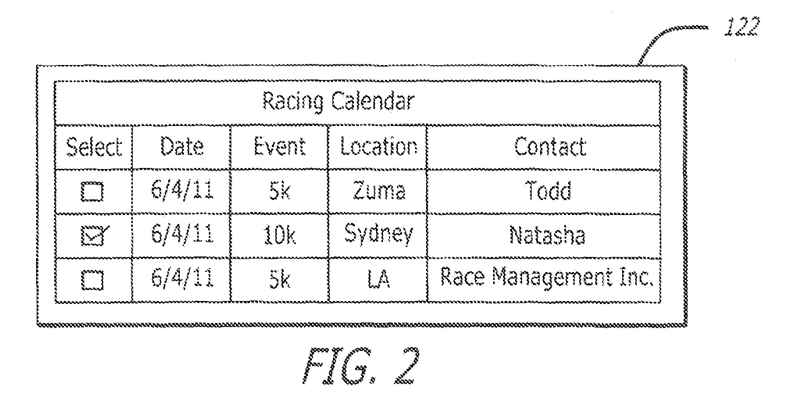
FIG. 2 is a preferred embodiment of a graphical user interface for use in generating an events calendar.
Figure 3:
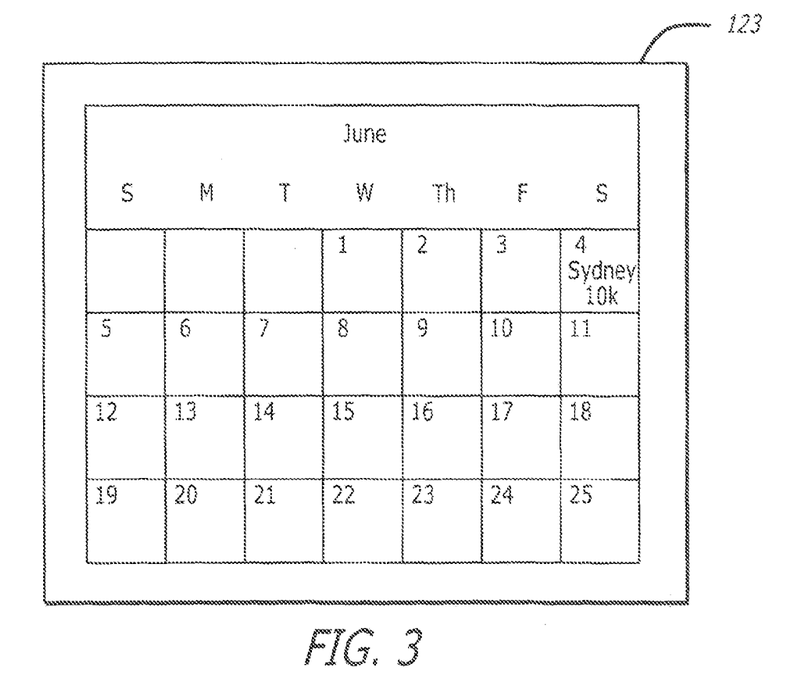
FIG. 3 is a front view of the events calendar generated by the graphical user interface of FIG. 2.

Referring to FIGS. 1 to 3, platform 102 preferably includes an events calendar 122 as one of its features. Processor 104 preferably is programmed to use information stored in events database 108 to generate a graphical user interface listing athletic events. The athletic events are preferably organized by event category, sub-category, date, event title, location and contact information.

The events calendar is preferably personalizable, i.e., a user may select desired events and organize the listing to include only the selected events. For example only, as shown in FIG. 2, the events calendar includes a means for selecting desired events, which in this example, includes a column of boxes, each box corresponding to a listed event, which the user may select by clicking on the box. Upon completing the desired selections, the user may instruct processor 104 to generate a calendar view 123 showing the selected events in a calendar format, such as shown in FIG. 3. The events calendar may send automated reminders to registered users of upcoming selected events. Such reminders may include one or more links to permit the user to access an event website or register for selected event. Calendar view 123 is preferably configured to be updated with additional or replacement desired events. Events listed in the events calendar and/or shown in the calendar view may include links to permit the user to access an event website or register for selected event.

Figure 4:
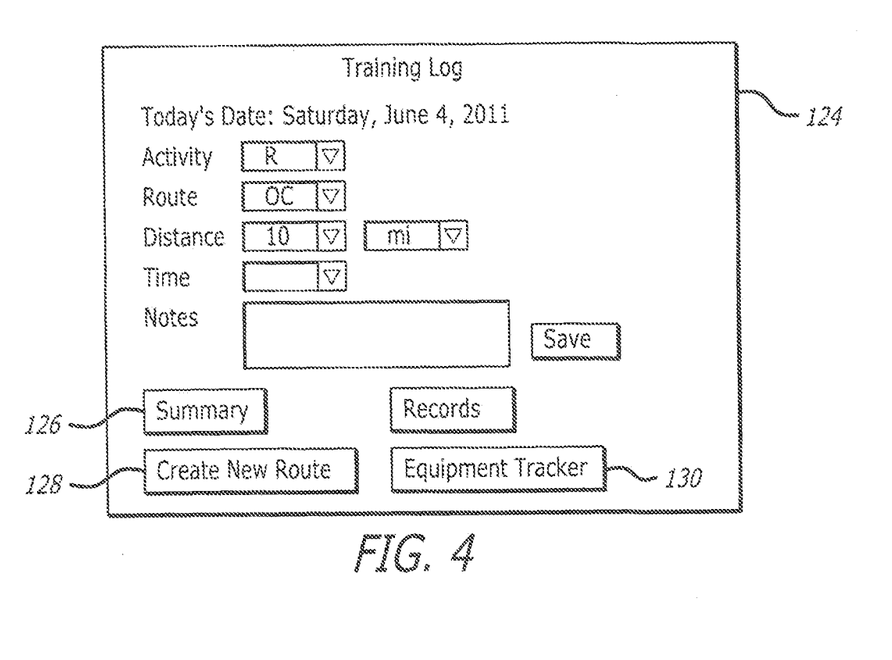
FIG. 4 is a preferred embodiment of a graphical user interface for use in generating a personal training log.

Referring to FIGS. 1 and 4, platform 102 preferably includes a training log 124 as one of its features. Processor 104 preferably is programmed to generate a graphical user interface having a plurality of fields and functions. The functions preferably include a "Summary" function 126 for summarizing training and/or racing data, a "Records" function for tracking a user's best performance data and an "Equipment Tracker" 130 for tracking the wear of various equipment used by the user. Each of these functions is described in greater detail below.

In order to optimize use of one or more of the functions, a user must enter data into the platform. As shown in FIG. 4, fields may be provided for date and activity. The date field may be automatically updated with the current date using the user's computer or mobile device. The activity field may be filled in or selected by the user from a predefined listing of activities, for example, running, swimming, biking, weight training, other, or racing. Each activity may be listed by its full name, or may be abbreviated to a single code (e.g., "R" for running, "B" for biking, etc.). A user may select from a menu the activity name or code for entry into the activity field. Once the user enters or selects the activity name or code, processor 104 generates additional fields for the user to fill in. The additional fields are preferably optimized for the particular activity selected. For example only, if running is the selected activity, the fields generated preferably include "Route," "Distance," "Time" and "Notes" as shown in FIG. 4.

The "Route" field may be an open field in which the user may enter a description of the training route, or may be configured to receive a route name or code corresponding to a route which the user previously described and stored, for example, using a "create new route" feature 128 described in greater detail below. For example, a user may describe and store a training route corresponding to the user's run along the ocean, and associate the route with a route name or code "OR." When the user subsequently enters information into the route field, the user may simply enter or select "OR" and the route information will be associated with the particular training log record being created. The "Distance" field preferably relates to the total distance the user traveled during the training activity. The "Distance" field may be automatically filled upon selection or entry of the route title or code, or modified independently of the route field. The "Time" field corresponds to the user's total training time for that activity. The "Notes" field is an open field which the user may enter notes regarding the training activity. Other fields may be added, for example, a heart rate field, a difficulty rating field, and/or a weather field.

For a swimming activity, processor 104 may generate fields relating to location, distance, time, notes and whether a wetsuit was used. For a biking activity, processor 104 may generate fields relating to route, distance, time, maximum speed, average speed, power and heart rate. As with the running activity, the "Route" field may be automatically filled upon entry or selection of the route name or code, or modified independently of the route field.

For the racing activity, processor 104 is preferably configured to generate fields relating to event category (e.g., running, biking, swimming, triathlon, duathlon, etc.), event sub-category and/or distance, splits, finish time, placing (over-all and age group) and notes. It will be appreciated that the number and type of activities may be varied as desired. Further, the number and type of fields may be modified as desired.

Figure 5:
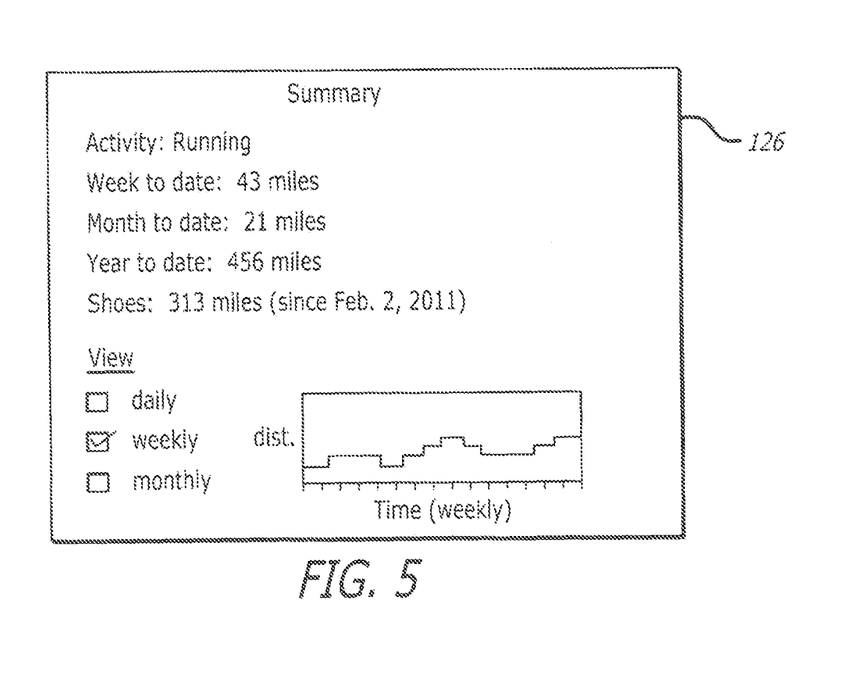
FIG. 5 is a preferred embodiment of a graphical user interface for use in generating a summary portion of the personal training log of FIG. 4.

Referring to FIGS. 4 and 5, the graphical user interface for training log 124 preferably includes a "Summary" function 126. Summary function 126 preferably automatically tracks and updates the user's data. In order to facilitate tracking of the user's data, the data stored for each field in database 118 is associated with a code, which processor 104 uses to maintain a running tally depending upon the type of code. Preferably summary function 126 is organized into racing activities and training activities.

Using running and biking as examples of training activities, processor 104 preferably updates a running tally for distance and time with each instance a new running or biking record is added to the user's training log. The running tally may be configured for one or more predetermined time periods. For example only, a running tally may be configured for weekly, monthly, annual, week-to-date, month-to-date and/or year-to-date for distance and/or time per an activity.

For example only, if a user desires to learn what their year-to-date distance is for biking, the user may select the "Summary" function and select a "Training Activities" function. The "Training Activities" function preferably generates an activity field. Selecting the activity name or entering the activity code into the field preferably generates a summary specific to the activity. For example, with running and biking activities, a training information field and a time period field will be generated. The user may then have the option of selecting one or more types of training information (e.g., distance and training time) for a selected time period (e.g., weekly, monthly, year-to-date, etc.). Upon making the selections, processor 104 generates a summary using the selection criteria entered by the user. The summary is preferably in a list form and preferably includes a graphical representation of the summary such as shown in FIG. 5.

Figure 9:
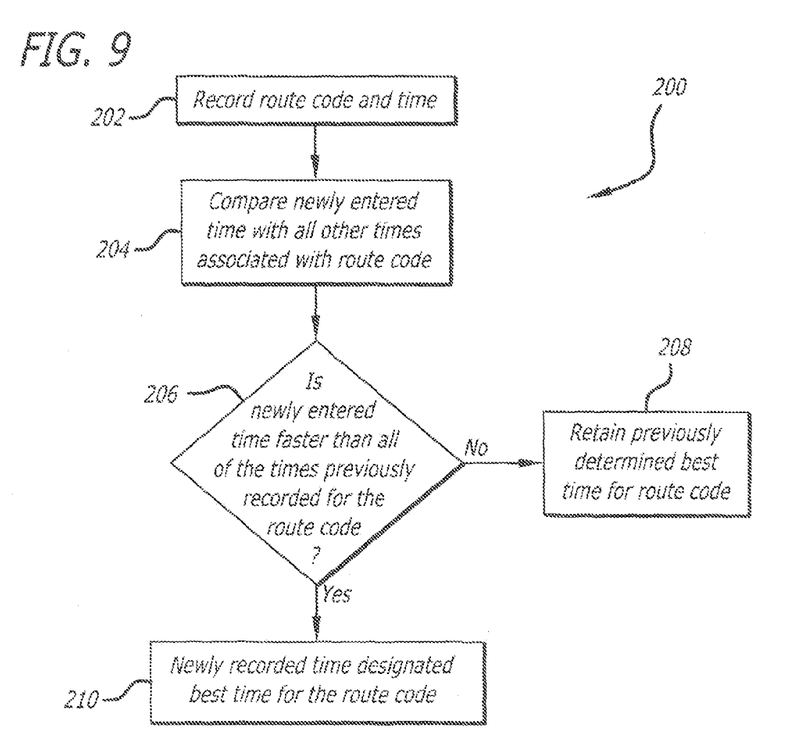
FIG. 9 is a logic diagram of a preferred method for tracking best training performances.

Referring to FIGS. 4 and 9, the training log preferably is configured with a "Records" function. The "Records" function preferably tracks a user's best performance data for a particular category of activity, for example, training and/or racing. For a training activity, the "Records" function, through processor 104 and training log database 118, stores the user's best performance record for a given activity. For example, for a training run where a user runs the "OC" route multiple times, each time the "OC" route is run by the user, the training time is entered by the user and processor 104 compares the newly entered time with prior times associated with the "OC" route. If a newly entered time for the "OC" route is less than any of the times currently of record for the "OC" route, the best time for the "OC" route is updated with the new best time and the date that the best time occurred.

FIG. 9 shows an exemplary method 200 for determining a user's best route time. In step 202, the user enters a route code and a time for completing the route. In step 204, the newly entered time is compared with all other times associated with the route code. In step 206, it is determined whether the newly entered time is faster than all of the times previously recorded for the route code. If the newly entered time is not faster than all of the previously recorded times for the time code, then in step 208 the previously determined best time is retained for the particular route code. If the newly entered time is faster than all of the times previously recorded for the route code, then in step 210 the newly recorded time is designated the best time for the route code, and the date that the best time occurred is updated.

It will be appreciated that the steps described above may be performed in a different order, varied, or certain steps omitted entirely without departing from the scope of the present invention.

If a user wishes to see what their best time is for a particular route, they may choose the running activity on a pull-down menu labelled "route." The pull-down menu will preferably be populated with the routes created from a "create new route" option 128, described in further detail below. When the user chooses a route from the pull-down menu, the records function will display the best time for that route and the date recorded for that time.

Similar best performance records may be maintained for times for other activities such as biking and swimming. Best performance records may be customized and maintained depending upon the training activity. For example, for running, biking and swimming, separate best performance records are preferably maintained for fastest time and longest distance. For biking in particular, best performance records are preferably additionally maintained for best average speed and best maximum speed. For swimming, best times may be recorded for set training distances.

Figure 10:
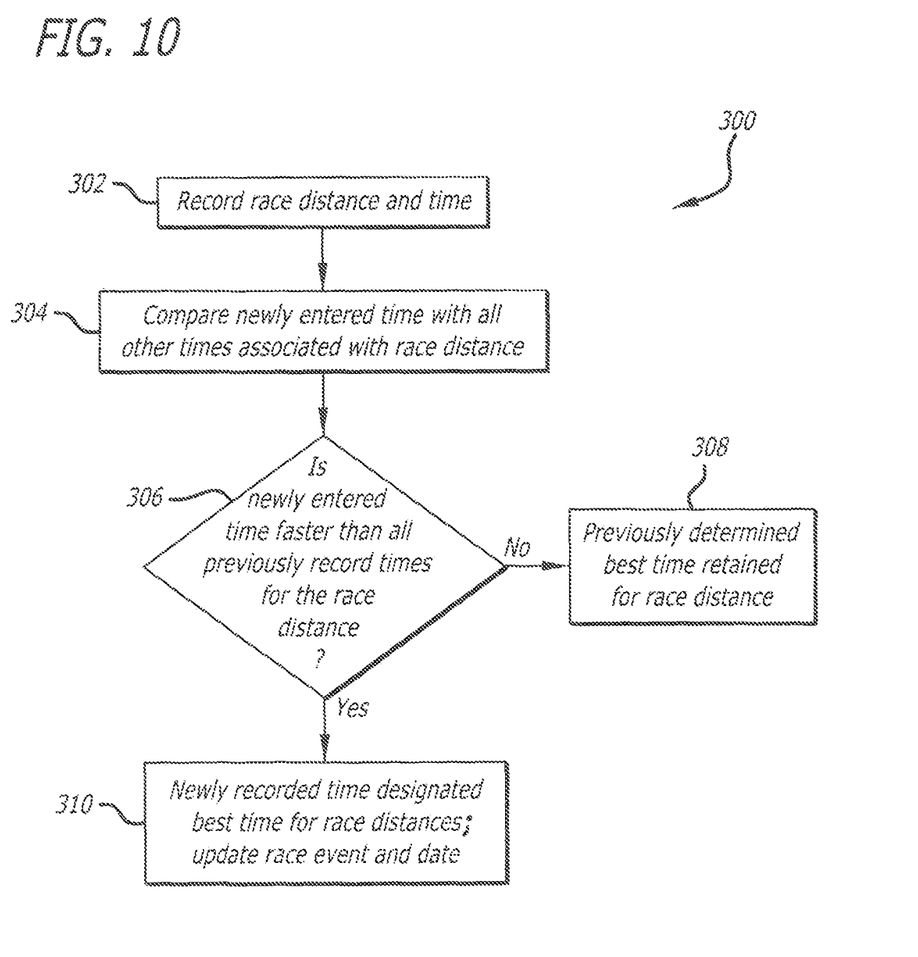
FIG. 10 is a logic diagram of a preferred method for tracking best racing performances.

If the category of activity relates to racing, the "Records" function is preferably configured to compare and update a user's best performance for a given race activity (e.g., running, biking, swimming, triathlon, etc.), sub-category and/or distance, splits, finish time, placing (over-all and age group) using methodology similar to that described above in relation to the training activity best records, but modified for the race environment. Examples of sub-categories of races for running include 5K, 10K, half-marathon, marathon, trailing running and track. Examples of races for cycling include road, track, cyclo-cross, mountain and BMX. Examples of sub-categories for races for swimming include open water and pool. Examples of sub-categories of races for multi-sport include triathlon (sprint, international, half-iron distance, iron distance), duathlon (sprint, international, long-distance), aquathon, aquabike, and off-road.

FIG. 10 shows an exemplary method 300 for determining a user's best race time. In step 302, a race distance and a time for completing the race is recorded. In step 304, the newly entered time is compared with all other times associated with the race distance. In step 306, it is determined whether the newly entered time is faster than all of the times previously recorded for the race distance. If the newly entered time is not faster than all of the previously recorded times for the race distance, then in step 308 the previously determined best time is retained for the particular race distance. If the newly entered time is faster than all of the times previously recorded for the race distance, then in step 310 the newly recorded time is designated the best time for the race distance, and the date and race event information that the best time occurred is updated.

It will be appreciated that the steps described above may be performed in a different order, varied, or certain steps omitted entirely without departing from the scope of the present invention.

A running tally on placings is preferably maintained. Placings may be maintained for over-all placing in a competition, placing within an age group (typically 5-year increments commencing from age 20), a "best placing percentage," and career wins. The "Records" function is preferably configured to determine the "best" placings of the user within a given race. For example, if a user places $150^{th}$ over-all out of a running race of 1,500 participants, the placing is preferably recorded as being in the top 10%. A subsequent placing of $100^{th}$ out of 2,000 participants is preferably recorded as being in the top 5% and designated as the new best race placing. Similar place-tracking may be maintained within age groups. For career wins, the records function may track the number of first place wins over the span of their athletic career. The records function may also track age-group wins (i.e., the number of times the user wins their age-group).

Figure 6:
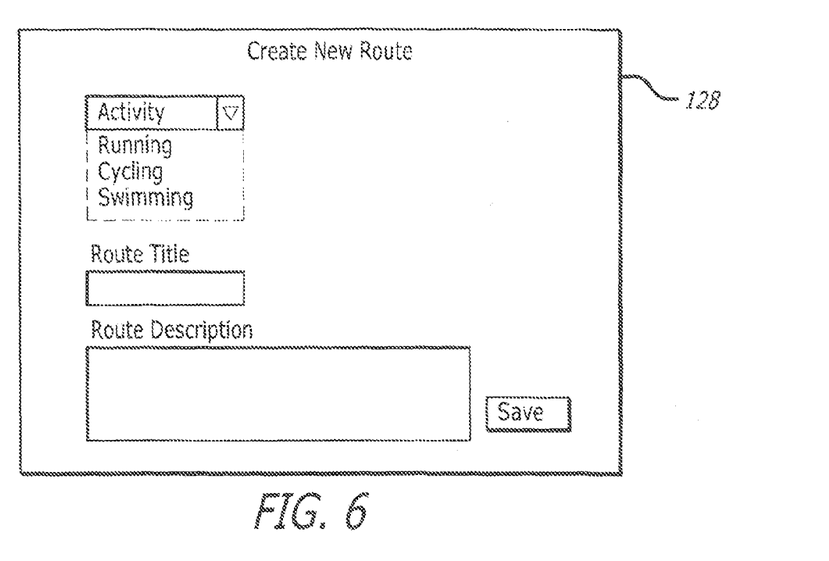
FIG. 6 is a preferred embodiment of a graphical user interface for use in creating a new route portion of the personal training log of FIG. 4.

Referring to FIGS. 4 and 6, platform 102 is preferably configured so that the user may create and record a route which may be used to later associate training data. Accessing link 128 will generate fields for the user to enter information pertaining to the route. A pull-down menu of activities such as running, cycling and swimming may permit the user to select an activity. Preferably, there will be two fields where the user enters information: a first field for entry of a route title or code, and a second one for entry of a route description. Once a route has been created and saved under the user-defined title or code, it will preferably be in a list of routes which will appear in the pull-down menu for the training log entries when entering training information.

Figure 7:
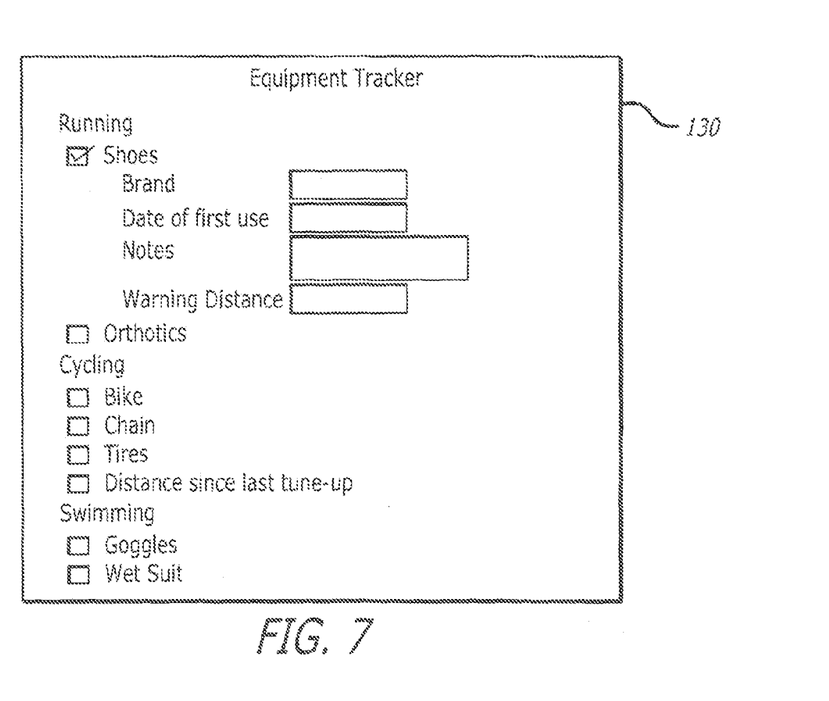
FIG. 7 is a preferred embodiment of a graphical user interface for use in generating an equipment tracker portion of the personal training log of FIG. 4.
Figure 11:
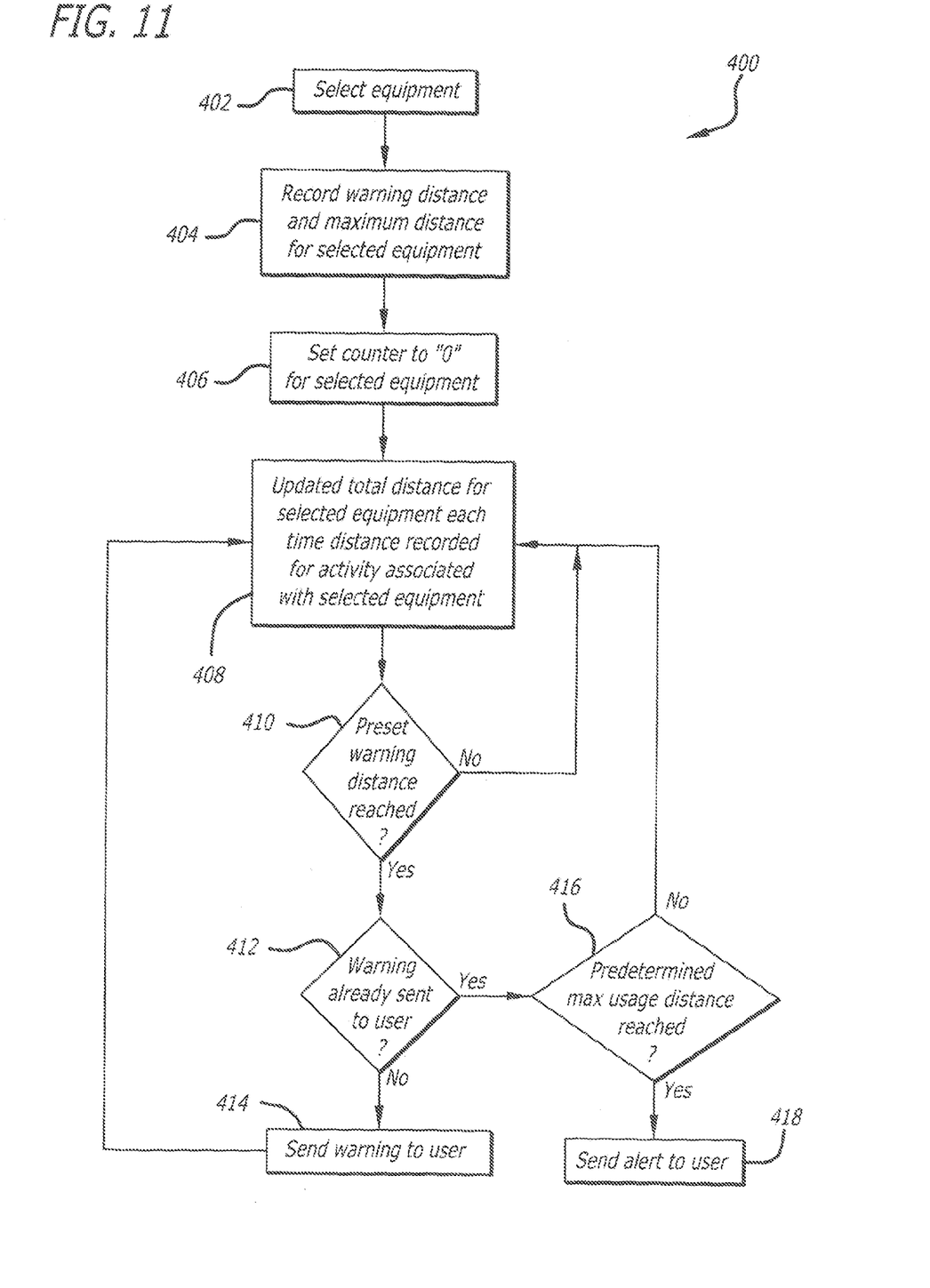
FIG. 11 is a logic diagram of a preferred method for tracking equipment usage.

Referring to FIGS. 4, 7 and 11, the training log is preferably configured with an "Equipment Tracker" function 130. Equipment tracker function 130 tracks usage of various equipment used by the user during training and/or racing activities. For example, for running, the equipment tracker function 130 is preferably configured to track usage of running shoes and/or orthotics. For shoes, fields for brand, date of first use, notes, and warning distance may be filled by the user. This feature will track distance according to the distance logged when the user enters a distance for their run based on the dated entered in the date of first use field. The warning distance feature will cause a warning message to appear next time the user logs into their training log. The warning message will appear when the tally for the distance matches the warning distance value entered by the user. If desired, the warning message may be electronically communicated over a network to the user, for example, by e-mail or texting. For orthotics, fields will preferably be available for date of first use, notes and warning distance.

For biking, the equipment tracker function 130 is preferably configured to track usage of one or more of a bike, a chain, a pair of tires, distance traveled since the last tune-up of the bike, cassette and odometer batteries. For the bike, fields will preferably be available for brand, date of first use, and notes. This feature will track distance according to the distance logged when the user enters a distance for their cycling based on the date entered in the date of first use field. For the chain, fields will preferably be available for date of first use, notes and warning distance. For tires, fields will preferably be available for date of first use, notes, warning distance. The tires category may be sub-divided into racing and training. For distance since last tune-up, fields will preferably be available for date of tune-up, notes and warning distance. This feature will track distance according to the distance logged when the user enters a distance for their cycling based on the date entered in the date of tune-up field. For the cassette, fields will preferably be available for date of first use and notes. For odometer batteries, fields will preferably be available for date of first use and notes.

For swimming, equipment tracker function 130 is preferably configured to track usage of a pair of swimming goggles, wetsuit and swimsuit. Usage may be based on distance, time or a combination thereof. For goggles, fields will preferably be available for brand, date of first use and notes. This feature will track distance according to the distance logged when the user enters a distance for their swimming based on the date entered in the date of first use field. For wetsuit, dates will preferably be available for brand, date of first use and notes. This feature will track distance according to the distance logged when the user enters a distance for their swimming based on the date entered in the date of first use field and the user checks the box for "wetsuit used" option appearing on either the swim training or swim racing (open water) screen. For swimsuit, fields will preferably be available for brand, date of first use and notes. FIG. 11 shows an exemplary method 400 of tracking equipment based on distance.

Referring to FIG. 11, in step 402, equipment from a predefined list for a given training and/or racing activity is selected. In step 404, a warning distance and a maximum distance are recorded for the selected equipment. In step 406, a counter is set for zero for the selected equipment. In step 408, the counter updates the total distance for the selected equipment each time a distance is recorded for the activity associated with the equipment. In step 410, it is determined whether the preset warning distance has been reached. If the preset warning distance has been reached, then in step 412, it is determined whether a warning has been sent to the user. If the warning has not been already sent to the user, then in step 414 a warning is sent to the user notifying the user that their equipment is approaching the maximum preset usage distance. If a warning has already been sent to the user, then in step 416, it is determined whether the maximum usage distance has been reached. If the maximum usage distance has not been reached, then the method repeats step 408. If the maximum usage distance has been reached, then in step 418, an alert is issued to the user notifying them that their equipment has reached the maximum preset usage distance.

The method described above may be configured to be based on usage time and/or calendar time if desired. Additionally, it will be appreciated that the steps described above may be performed in a different order, varied, or certain steps omitted entirely without departing from the scope of the present invention. For example only, warning messages regarding an approaching maximum usage distance or time may be omitted if desired.

It will be appreciated that programmed functions of the training log may be varied as desired. One or more of the functions described above may be omitted, or additional functions may be programmed into the training log. Moreover, though described in relation to running, swimming, biking and triathlons, it will be appreciated that the training log may be adapted for other activities.

As shown in FIG. 1, platform 102 preferably includes a rankings generator 120. Rankings generator 120 preferably is configured to compare participants in one or more competitions based on a number of criteria including, for example, event category, event sub-category, eligibility, gender and age. Event category relates to the type of sporting competition (e.g., running, swimming, biking, triathlon, duathlon, etc.). Event sub-category relates to the distance and/or type of event within the sport. For example, for running, relevant sub-categories may include 5K, 10K, marathon, etc. For swimming, relevant sub-categories may be based on distance, type of stroke, and/or relay or individual. Eligibility is preferably based on one or more criteria, for example, a predefined geographical region and whether a participant has completed a predetermined number of competitions. Gender is explanatory. Age preferably relates to age group, which typically is grouped in increments of 5 years.

Rankings generator 120 preferably compares participants based predominately on head-to-head ("H2H") matches. H2H comparison provides one of the best forms of rankings since rankings, in their most basic form, are meant to compare one entity against another. Rankings relying less on H2H are less accurate in terms of truly ranking entities among one another since more theory must be relied upon.

Figure 12:
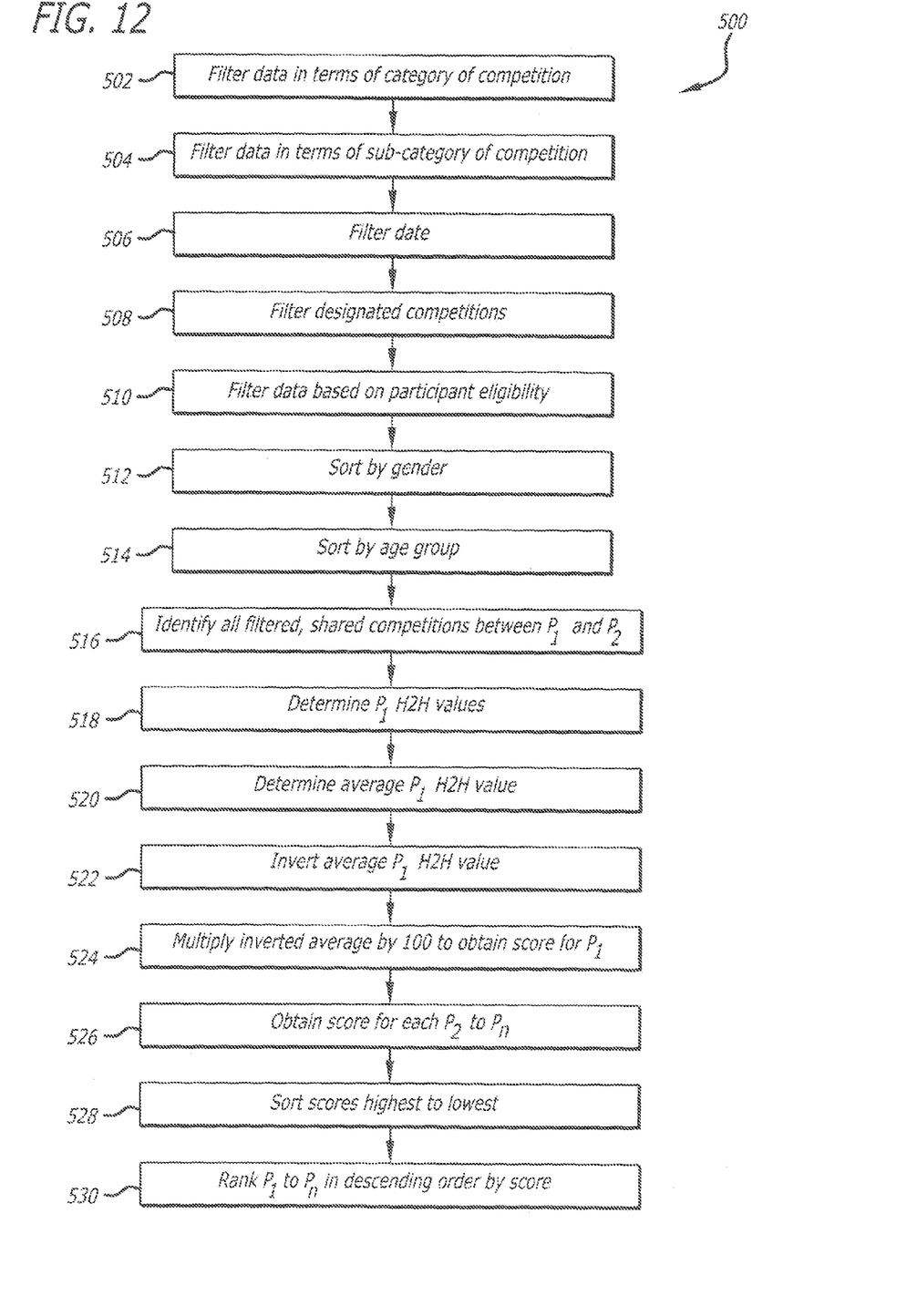
FIG. 12 is a logic diagram of a preferred method for ranking a participant in a competition against other participants.
Figure 13:
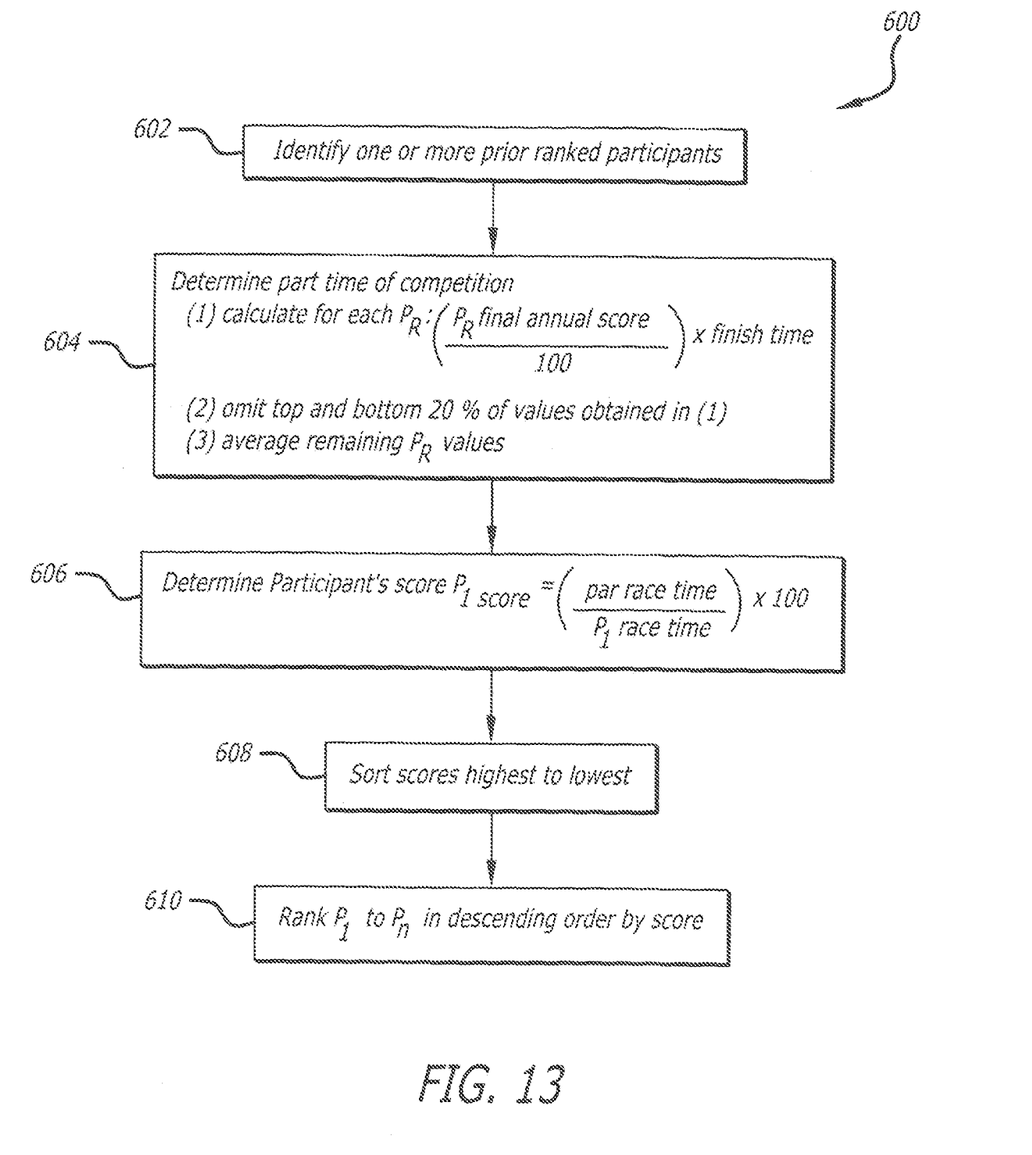
FIG. 13 is a logic diagram of another preferred method for ranking a participant in a competition against other participants.

FIG. 12 shows an exemplary method 500 of ranking multiple participants ($P_n$) in one or more competitions. For purposes of this example, the competition will be a running race, though it will be appreciated that the method may be applied as desired to other categories of competition.

Preferably upon receiving results data for a new competition and storing those results with other results data in results database 110, in step 502 the data is filtered in terms of category of competition. For example, if the competition relates to a running race, the scope of the rankings will be narrowed to those involving runners. In step 504, the data is filtered in terms of a sub-category of competition. For example, if the running race is a half-marathon, the rankings will be limited to races involving half-marathons. In step 506, the date of the competition is filtered to narrow the rankings to half-marathons taking place within a predetermined period of time, for example, calendar year to date. Next, in step 508, the results are filtered in terms of whether the competition is a designated race. For example, certain competitions may be designated for use in rankings, while other competitions may be excluded by not designating them for use in rankings. Designations may also be used to filter competitions based on geographical area to localize rankings.

In step 510, the results are filtered based on participant eligibility. Participant eligibility preferably is determined based geographical residence of a participant, and/or whether the participant has completed a pre-determined minimum number of competitions matching the filtered criteria set forth above. Geographical eligibility may be defined by a radius within a particular city, by a natural area or region, or by a radius within a participant's residence. Eligibility based on a pre-determined minimum number of competitions helps to ensure that a participant who performs well in a single competition does not unfairly remain highly ranked should that participant choose not to compete in any more competitions for the rest of a given time period (e.g., year). It is preferred that the threshold for eligibility be set for 3 competitions, though this number may be varied more or less as desired.

In step 512, results are sorted based on gender. In step 514, the results are preferably sorted based on age group. In step 516, all filtered, shared competitions between a first participant ($P_1$) and a second participant ($P_2$) are identified. In step 518, singular $P_1$ H2H values are determined. That is, if $P_1$ beat $P_2$ more often than not, then the $P_{1v2}$ value will equal 1. If $P_1$ lost to $P_2$ more often than not, then the $P_{1v2}$ value will equal 2. If neither of the above is true, then the $P_{1v2}$ value will equal 0. Step 518 is repeated for $P_1$ for each additional $P_n$.

In step 520, the average $P_1$ H2H value is determined by summing all of the $P_1$ H2H values calculated in step 518, and dividing the result by (n−1), where n=number of filtered and sorted participants. In step 522, the average is inverted. In step 524, the result is multiplied by 100 to obtain a score between 50 and 100. In step 526, steps 516 to 524 are repeated for each filtered and sorted participant to obtain a score for each participant. In step 528, the scores are sorted from highest to lowest to obtain a ranking, with the highest score in step 530 being ranked first for the particular geographical region, event category, event sub-category, gender, and age group.

It will be appreciated that the steps described above may be performed in a different order, varied, or certain steps omitted entirely without departing from the scope of the present invention. For example, rankings need not be based on geographical region. Additionally, rankings may be based on over-all rankings in addition to, or in place of age group rankings. The sub-category of events may be modified depending upon the category of sport. For example, in a swim meet, more than one sub-category may exist, such as distance, stroke, and/or relay. Steps 522 to 524 may be omitted by taking a ranking based on the raw score.

Some steps may be combined. For example, steps 520 to 524 may be combined according to the following formula:

Score=((n−1)/Σ$P_1$H2H values)×100 where n=the number of filtered and sorted participants.

The following example is set forth below utilizing the above rankings method.

EXAMPLE

Participants $P_1$, $P_2$, $P_3$ and $P_4$ participate in a series of 5K running races between January 1 to June 1 in the 35-39 year old age group. The minimum number of races a participant must complete to be eligible for ranking is three. Their race placing within the 35-39 year old age group for each race is shown in the table below.

| Participant | Race 1 Placing | Race 2 Placing | Race 3 Placing |
|---|---|---|---|
| $P_1$ | 2 | 3 | 2 |
| $P_2$ | 3 | 2 | 3 |
| $P_3$ | 4 | 1 | 1 |
| $P_4$ | 1 | | |

The race results have been added to the results database and filtered according to geographical area, event category and sub-category, gender and age group. $P_1$ to $P_4$ live in the same pre-defined geographical area. However, $P_4$ participated in only one race. Accordingly, $P_4$ is ineligible for rankings.

For $P_1$ v $P_2$ H2H matches, $P_1$ beat $P_2$ two out of three times. Accordingly, $P_1$ beat $P_2$ more often than not. Thus, the $P_{1v2}$ value will equal 1.

For $P_1$ v $P_3$ H2H matches, $P_1$ beat $P_3$ one out of three times. Accordingly, $P_1$ lost to $P_3$ more often than not. Thus, the $P_{1v3}$ value will equal 2.

The average $P_1$ H2H values is equal to the sum 1+2, divided by (n−1), where n=the number of filtered and sorted participants. In the present example, it will be assumed that there were only three eligible participants in all three races. Thus, the average $P_1$ H2H value is 3/2=1.5. Inverting this number and multiplying by 100 gives $P_1$ a score of 66.67.

For $P_2$ v $P_1$ H2H matches, $P_2$ beat $P_1$ one out of three times. Accordingly, $P_2$ lost to $P_1$ more often than not. Thus, the $P_{2v1}$ value will equal 2.

For $P_2$ v $P_3$ H2H matches, $P_2$ beat $P_3$ one out of three times. Accordingly, $P_2$ lost to $P_3$ more often than not. Thus, the $P_{2v3}$ value will equal 2.

The average $P_2$ H2H value is equal to the sum 2+2, divided by 2. Thus, the average $P_2$ H2H value is 4/2=2.0. Inverting this number and multiplying by 100 gives $P_2$ a score of 50.00.

For $P_3$ v $P_1$ H2H matches, $P_3$ beat $P_1$ two out of three times. Accordingly, $P_3$ beat $P_1$ more often than not. Thus, the $P_{3v1}$ value will equal 1.

For $P_3$ v $P_2$ H2H matches, $P_3$ beat $P_2$ two out of three times. Accordingly, $P_3$ beat $P_2$ more often than not. Thus, the $P_{3v2}$ value will equal 1.

The average $P_3$ H2H value is equal to the sum 1+1, divided by 2. Thus, the average $P_3$ H2H value is 2/2=1.0. Inverting this number and multiplying by 100 gives $P_3$ a score of 100.00.

Ranking highest score to lowest ranks $P_3$ first, $P_1$ second, and $P_2$ third.

Should $P_4$ later run two more 5K races meeting the filtered criteria, $P_4$ will become an eligible participant. At that point, $P_4$'s results will preferably be retroactively factored into the rankings to rank $P_4$ among other filtered and sorted participants.

Other methods of ranking may be used instead of, or in combination with the above rankings method. For example, FIG. 10 shows a method 600 that utilizes a prior ranked participant ($P_R$), and relies on finish times to generate a ranking. In step 602, for a given competition, one or more prior ranked participants are identified. In step 604, a par time for the particular competition is determined by first dividing the prior final annual score of each prior ranked participant by 100 and multiplying the result by the finish time of each prior ranked participant. Secondly, in step 604, preferably the top and bottom 20% of $P_R$ finish times are omitted from the competition. Third, in step 606, the remaining $P_R$ finish times are averaged to generate a par finish time for the competition. Steps 602 to 606 may be summarized as follows:

(1) calculate for each $P_R$ the following:

$$(P_R \text{ final annual score}/100) \times \text{finish time};$$

(2) omit preferably the top and bottom 20% of $P_R$ values obtained in (1); and (3) average the remaining $P_R$ values to obtain the par race time.

In step 608, a participant's score is calculated as set forth below:

$$P_1 \text{ score} = (\text{par race time}/P_1 \text{ race time}) \times 100$$

It will be appreciated that the steps described above may be performed in a different order, varied, or certain steps omitted entirely without departing from the scope of the present invention. For example, the percentage of omitted $P_R$ values used to determine the par race time may be varied more or less than the 20% indicated above, for example, 15% or 10%.

If desired, the method 600 may be combined with method 500 by adding the score obtained from each method for a particular participant, and dividing the result by two. The resulting score will give the participant a rank that is weighted towards a H2H factor.

Other methods for ranking individuals may be used as desired. For example, rankings based on point totals may be used. In such a method, a series of designated races are each assigned point totals for a predetermined number of places (over-all and/or placing within each age group). The highest ranked participant is that who has the most points at the end of the period of time, or when all of the races have been conducted.

Rankings generator 120 may be configured to rank participants in a wide variety of sports in addition to those already mentioned, for example only, golf, tennis, martial arts and other sports.

Figure 8:
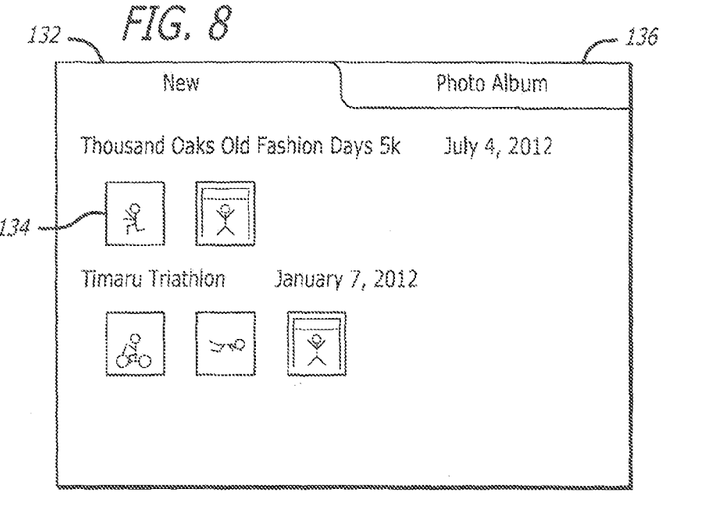
FIG. 8 is a preferred embodiment of a graphical user interface for use in generating a media portal permitting a user to access and purchase media content.

Referring to FIGS. 1 and 8, platform 102 may be configured to permit media content providers to upload to media database 114 media specific to a registered user, which the registered user may access once logged-in. For example, a third party, such as a photographic company, may upload pictures taken of the registered user during one of the competitions in which the registered user participated. Preferably, the pictures or photos are tagged (associated) with the individual or individuals in the photo. Photos may be tagged, for example, by noting a race number or other identifier worn by the person in the photo, obtaining personal or contact details recorded with the race number, and matching the person in the photo with the personal or contact details corresponding to the race number. The uploaded photo is preferably initially a "thumbnail" photo 134 (with embedded link) to the source or website of the entity providing the photo.

Matching a registered user of the platform with their photo is preferably by competition, user name, zip code and age, preferably in that order. In particular, the photo company would forward a listing to the platform of participants for a particular race where the company took photos. Processor 104 compares the list provided by the photo company against the listing of register users of the platform. Positive matches are identified and a match list is created and forwarded to the photo company. The photo company then provides the thumbnail photos and/or links for the positive matches to the platform, and those are associated with the registered users and/or subscribers using the record identifiers of the registered users and/or subscribers.

Subsequently, the registered user may log into the platform and access the photos. The registered user may click on the "new" tab 132 and see a collection of their photos from different races. If the registered user and/or subscriber desires to purchase the photo, they may select the image and/or link and go to the photo company's website to make the transaction. The selection may be made by clicking or otherwise interacting with the image and/or link. Once purchased, the user may transfer and/or download the photo to their digital photo album (under the "photo album" tab 136). The media may be organized by registered user, date and competition.

It will be appreciated that images other than thumbnail photos may be used, including icons or symbols. Preferably, the thumbnail photos are copy-protected so that the registered user cannot copy without first purchasing them. If desired, the thumbnail image may be "unlocked" to permit the user to transfer it to the user's digital photo album. Alternatively, once purchased, the photo may be downloaded from the photo company. In a preferred embodiment, the media available for purchase is limited only to photos taken of the registered user during a competition in which the registered user participated. In other situations, a photo company might associate a video clip with a registered user.

If desired, any commercial transaction to purchase the media may be conducted by platform 102. For example, if a user is interested in purchasing media content in which their image appears, the user may access a link associated with the thumbnail image of interest. The activated link will bring the user to a page where the user may order the media. Thereafter, the user may select a delivery option, such as e-mailing the media content to the user's e-mail account, or transferring the media content to a limited access area associated with the user's account on platform 102, such as photo album 136 in FIG. 8.

It will be appreciated that the media portal described above may be configured in a variety of ways. For example, instead of sending a match list to a third party media content provider, third party media content providers may send the media content, or a link to media content locally stored by the third party, to platform 102, which will accept tagged media content or links which match users registered on platform 102 and reject tagged media content or links that do not match users registered on platform 102.

Platform 102 is preferably programmed to automatically notify a registered user, more preferably, a subscriber, upon the uploading of results into results database 110. Platform 102 is further preferably configured to automatically notify a registered user upon the availability of media specific to the registered user. The media may become available upon uploading the media to the media database, or by a media content provider leaving an indication in the registered user's account that the media is available for access through a link to the media provider's website.

The foregoing description is by way of example only, and may be varied considerably without departing from the scope of the present invention. For example only, the platform may be optimized for use with hand-held mobile devices. For example, a registered user may access their own training log while at the gym or immediately after a workout and update their training log remotely. Additionally, the training log may be updated automatically with a GPS device in sync with training log feature 124. For example, a cyclist or runner may wear a GPS-enabled device which is Internet ready so that as the user is training, training data is being communicated "live" to the user's personal training log on the platform. Upon finishing the training activity, the user may access a summary of the training activity. It will be appreciated that the device may communicate with the platform only after the training activity is complete to do a data dump in order to reduce Internet usage.

The "Summary" function may be modified to provide visual representations of training history in terms of pie charts and other visual aids. Additional fields may be added for weight, heart rate, difficulty rating and weather if desired. Annual reports may be generated and printed for each registered user as desired.

The "Equipment Tracker" function may be modified to allow a user to enter their own equipment for tracking. Additionally, a "notes" field may be provided to permit the user to describe the brand of equipment, or other information as desired by the user. The warning distance feature may be configured to send a notification to the user via an electronic communication such as e-mail or texting.

The personalized calendar feature may be configured to determine if a registered user is within a predetermined distance from a competition, and provide the user with information regarding hotels and restaurants within a predetermined radius of the site of the competition. For example, if a registered user lives 75 miles away from a competition for which the user entered, the platform may send or e-mail the user information on all hotels within a 5 mile radius of the site of the competition. Moreover, the platform may be configured to determine vacancy information for the hotels and provide the user with hotel information for hotels still having vacancy. The platform may be configured to notify a registered user of the forecasted weather at the site of the competition a set number of days before the competition, for example, one, two and/or three days before the competition date. The weather forecast may include hourly forecasts if desired.

The platform may be configured for use with activities other than running, cycling, swimming or multisport. For example only, the platform may be configured for use with weight training, kayaking, crew, hiking, mountain climbing, golf, tennis, martial arts, and other sports.

Information normally stored at a physical location may be stored in a cloud, considerably reducing the hardware needed for memory requirements often associated with large volumes of data.

The features described with respect to one embodiment may be applied to other embodiments, or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for matching media content created by a third party at an athletic event with a participant in the event, said system comprising:
   a database server having a user database for maintaining records of users registered to access said database server; and
   a processor configured to receive a listing of participants whose images appear in media content created at the athletic event, compare the listing with the registered users based on the records maintained in said user database, and generate a match list of participants whose images appear in the media content created at the athletic event and who are registered users, said listing of participants whose images appear in the media content including at least a name and zip code for each participant, said records of registered users each including at least the registered user's name and zip code, said processor being configured to generate said match list by comparing the names and zip codes on said listing with the names and zip codes in said records.

2. The system of claim 1, wherein said processor is configured to send the match list to the third party, and receive from the third party at least one link linking a matched registered user with the media content showing the registered user's image.

3. The system of claim 1, wherein said processor is configured to permit a registered user access to the media content if the registered user is listed on the match list.

4. The system of claim 1, wherein the listing of participants comprises a link for each listed participant to the media content, each link being tagged with data identifying the participant.

5. The system of claim 1, wherein the media content consists of one or more photographs of the participant.

6. The system of claim 1, wherein said processor is configured to send an electronic communication to a registered user to notify the registered user that media content showing the registered user's image is available for viewing by the registered user, the electronic communication being sent to the registered user based on contact details stored on said user database.

7. The system of claim 1, wherein said processor is configured to direct a registered user who appears on the match list to a payment gateway so that the registered user may purchase the media content tagged with the registered user.

8. The system of claim 7, wherein said database server comprises a media database for maintaining media content purchased by the registered user.

9. The system of claim 8, wherein the media content purchased by the registered user is maintained in a digital photo album associated with the registered user, said payment gateway including a delivery option for transferring the purchased media content to the digital photo album associated with the registered user.

10. The system of claim 7, wherein said payment gateway includes a delivery option for delivering purchased media to the registered user.

11. The system of claim 10, wherein the delivery option includes e-mailing the purchased media content to an e-mail account associated with the registered user.

12. The system of claim 10, wherein the delivery option includes transferring the purchased media content to a digital photo album associated with the registered user.

13. The system of claim 1, further comprising a training log server configured to:
receive and store data from each registered user regarding a category of athletic activity in which the registered user engaged;
receive and store data from each registered user regarding a distance the registered user trained for a given day for each category of athletic activity;
receive and store data from each registered user regarding an amount of time the registered user trained for each category of athletic activity;
calculate a time-based total distance for each category of athletic activity; and
generate a graphical representation of at least one of the calculated time-based total distances.

14. The system of claim 13, wherein said training log server is configured to associate the time data with a route identifier associated with a route created by the registered user, said training log server configured to determine the lowest time for each route created by the registered user.

15. The system of claim 13, wherein said training log server is configured to receive and store data from each registered user regarding a first use of a bike used by the user since the bike received a tune-up, and track a distance the bike is used based on the data received from the registered user regarding the distance the registered user trained on the bike.

16. The system of claim 13, wherein said training log server is configured to be updated as the registered user is training by a GPS-enabled device synced with said training log server.

17. A method for matching media content created by a third party at a sporting event with a participant of the sporting event using a computer web-based platform, the platform having a database server with a database of users registered with the platform, the method comprising:
receiving, at the platform, a listing of participants of the sporting event, each participant being tagged with media content created by the third party, the listing of participants including at least a name and zip code for each participant;
comparing the listing of participants with a listing of users registered with the platform to generate a match list of registered users who were participants in the sporting event and are tagged in media content, the listing of registered users being maintained in the database, the listing of registered users including at least the registered user's name and zip code;
forwarding the match list to the third party;
receiving from the third party a plurality of links, each link linking a registered user with media content tagged with the registered user; and
generating a graphical user interface that permits the registered user to access the link to the media content tagged with that registered user, the match list being generated by comparing the names and zip codes in the listing of participants with the names and zip codes in the listing of registered users.

18. The method of claim 17, further comprising linking the registered user with the media content tagged with the registered user, the tagged media content being stored at a remote site controlled by the third party.

19. The method of claim 17, further comprising receiving an indication from the third party that the media content was purchased by the registered user, and storing the media content to a restricted personal area of the platform requiring a log in by the registered user.

20. The method of claim 17, wherein the generation of the graphical user interface includes displaying a thumbnail image of the media content tagged with the registered user, the link being embedded with the thumbnail image.

21. The method of claim 17, further comprising receiving an indication that the registered user wants to purchase the media content, and directing the registered user to a payment gateway to purchase the media content.

22. The method of claim 21, further comprising providing the registered user with a delivery option to deliver media content purchased by the registered user.

23. The method of claim 21, further comprising e-mailing purchased media content to an e-mail account associated with the registered user.

24. The method of claim 21, further comprising transferring purchased media content to a digital photo album associated with the registered user.

* * * * *